United States Patent [19]

Garnick

[11] Patent Number: 5,019,381

[45] Date of Patent: May 28, 1991

[54] METHOD FOR LOWERING CHOLESTEROL LEVELS USING GM-CSF

[75] Inventor: Marc Garnick, Brookline, Mass.

[73] Assignee: Genetics Institute, Inc., Cambridge, Mass.

[21] Appl. No.: 170,478

[22] Filed: Mar. 21, 1988

[51] Int. Cl.$^5$ .............................................. A61K 37/02
[52] U.S. Cl. ..................... 424/85.1; 514/2; 514/8; 514/12; 514/21
[58] Field of Search ................ 424/85.1; 514/2, 8, 514/12, 21

[56] References Cited

PUBLICATIONS

Pharmacia Catalog, 1983, pp. 52–61, "Affinity Chromatography".
Marx, Science, 248, 1990, p. 1492.
Whetton et al, EMED, vol. 5, 1986, pp. 3281–3286.
Stober et al., Biological Abst. #67397, vol. 72, 1981.
Brown et al., Ann. Review Biochem., 52: 223 (1983).
Brown et al., Science, 232: 34–47 (1986).
Clark et al., Science, 236: 1229–37 (1987).
Dixon et al., Clin. Res. U.S.A., 30(3): 707a abstract (1982).
Dixon et al., Metabolism, 33(5): 400–4 (5/84).
Dodge et al., Exp. Molec. Path, 36:44–56 (1982).
Fogelman et al., J. Immunol., 131: 2368–73 (1983).
Garnick et al., Natl. Amer. Fed. Clin. Res., 37:260A (1989).
Gould et al., Medical Letter: 87–90 (1987).
Havel et al., J. Clin. Invest., 81: 1653–60 (1988).
Kokkonen et al., PNAS U.S.A., 84: 2287–91 (1987).
Leslie et al., Biochim. Biophys. Acta, 711(2): 290–3034 (1982).
Marx, Jean L., Science, 239: 257–8 (1/15/88).
Motoyoshi et al., Lancet: 326 (8/5/89).
Nimer et al., JAMA, 260(22): 3297–3300 (12/9/88).
Pfeffer et al., PNAS U.S.A., 82(8): 2417–21 (4/85).
Rifkin et al., Behring Inst. Mitt, 83, 125–133 (8/88).
Shimano et al., Circulation, 80: 0321 (Oct. 1989).
Wilson et al., Fed. Proc. U.S.A., 43(4): #3267 (1984).
Wilson et al., J. Clin. Oncol., 7(10): 1573–7 (10/89).
Fogelman et al., Proc. Nat. Acad. Sci., U.S.A., 79:922–926 (1982).
Sieff et al., Science, 230: 1171–1173 (1985).
Wong et al., Science, 228: 810 (1985).

Primary Examiner—Garnette D. Draper
Attorney, Agent, or Firm—Luann Cserr; Bruce Eisen

[57] ABSTRACT

Methods are presented for lowering levels of lipoprotein cholesterol, serum cholesterol and other lipids comprising the administration of M-CSF or GM-CSF.

1 Claim, No Drawings

METHOD FOR LOWERING CHOLESTEROL LEVELS USING GM-CSF

INTRODUCTION

Hyperlipoproteinemia denotes a class of physiological conditions in which there exist greater than normal levels of lipoprotein in blood, plasma, or serum. The class consists of acquired hyperlipoproteinemia, a persistently greater than normal plasma concentration of lipoproteins that is nonhereditary in cause and secondary to some other disorder such as myxedema, and familial hyperlipoproteinemia, which is any of several genetic disorders of lipid metabolism characterized by increase in concentration of one or more types of serum lipoprotein. The particular disorders encompassed by the term hyperlpoproteinemia are set forth in the *International Dictionary of Medicine and Biology* 1365 (1986). Familial hyperlipoproteinemia includes several forms of hypercholesterolemia, e.g. essential hypercholesterolemia and familial hypercholesterolemia. Hypercholesterolemia generally describes an elevated level of cholesterol in the blood or blood serum. Also included within the hyperlipoproteinemias are the hyperlipidemias, generally defined as a greater than normal concentration of lipids in blood plasma, and including carbohydrate-induced hyperlipidemia, combined fat- and carbohydrate-induced hyperlipidemia, fat-induced hyperlipidemia, and mixed hyperlipidemia.

A great deal of attention has focused on the search for agents that safely and effectively reduce levels of lipoprotein, other lipids, and particularly cholesterol in the blood. Elevated levels of blood cholesterol increases an individual's risk of encountering coronary heart disease. While blood cholesterol levels can be somewhat reduced through diet modifications, recourse to drug therapy is often required.

Coronary heart disease is caused by atherosclerosis which results from the formation of atherosclerotic plaques. These plaques are build-ups of cholesterol deposited in the arterial wall. The build-up occurs because cholesterol is insoluble in water and thus not readily removed. Thus, "[i]f cholesterol is to be transported safely in blood, its concentration must be kept low and its tendency to escape from the bloodstream must be controlled." M. S. Brown and J. L. Goldstein, *Science*, 232:34–47 (1986).

Cholesterol is transported in the body largely through the interaction of the lipoproteins. Initially, free cholesterol is bound to the surface of high density lipoproteins (HDL) and coupled to a fatty acid in an esterification reaction. The cholesteryl esters which are formed on the surface of HDL are subsequently encapsulated within low density lipoproteins (LDL). The cholesteryl ester-containing LDL then enters certain cells through a lipoprotein-specific receptor-mediated-endocytosis. Once inside the cell, the esters are hydrolyzed back to cholesterol and put to constructive use in the formation of steroids, membranes and bile acids.

The LDL is the most abundant cholesterol carrying lipoprotein in the human body and carries about three-fourths of the total cholesterol of normal human plasma. Lowering plasma LDL levels will effect a reduction of serum cholesterol and so decrease the progression of atherosclerosis. Futhermore, because the HDL remove free cholesterol from the plasma and prepare it for encapsulation within the LDL a high HDL/LDL ratio is generally preferred.

THE INVENTION

The invention provides a method for lowering lipoprotein cholesterol levels, lipoprotein levels and levels of other lipids comprising administering to a primate a cholesterol-reducing amount of M-CSF or GM-CSF. As used herein the term primate includes humans, apes and monkeys.

It is contemplated that this invention will specifically lower the cholesterol-rich LDL levels, as compared to the less harmful HDL levels, and so reduce the likelihood that the primate undergoing treatment will encounter coronary heart disease. Thus, the method of this invention will lower serum levels of cholesterol and other lipids.

The preferred embodiment involves the use of M-CSF, also known as macrophage colony stimulating factor. M-CSF produces colonies which contain primarily macrophages. It has been described in Kawasaki et al., *Science*, 230:291–296 (1985) and publications by E. R. Stanley. Its production by recombinant DNA techniques is described in U.S. application Ser. No. 860,377. A truncated version is described in PCT/US86/00238.

GM-CSF, also known as granulocyte-macrophage colony stimulating factor may also comprise the therapeutic component of this invention. It is described in detail in Wong et al., *Science*. 228:810–815 (1985) and references cited therein. Wong et al. also teach its production via recombinant DNA techniques.

The M-CSF and the GM-CSF employed in this invention include the natural proteins, recombinant versions thereof, and derivatives and analogs thereof, which may contain amino acid deletions, substitutions and/or insertions, but which retain the characteristic biological activity and are encoded by cDNAs capable of hybridizing to cDNAs for the naturally occurring versions. Also included, of course, are naturally-occurring isotypes or allelic variations in the protein or its coding sequence resulting from expression of the protein in different members of a species.

The components of this method can be systemically administered parenterally, e.g. intravenously. Where desired for treatment it may also be possible to administer one or more components of the method subcutaneously. When systemically administered, the therapeutic preparations for use in this invention are in the form of pyrogen-free, parenterally acceptable aqueous solutions.

The dosage regimen involved in the use of these compositions will be determined by the attending physician considering various factors which modify the action of drugs, e.g., the condition, body weight, sex, and diet of the patient, the severity of the condition, time of administration and other clinical factors. The M-CSF and the GM-CSF should be administered in a dose insufficient to cause a systemic toxic reaction, but sufficient to elicit the desired pharmacological response.

A therapeutic dose is in the range of 20–200 micrograms(ug)/kg/day of M-CSF or 0.5–30 ug/kg/day of GM-CSF. The dosages cited above may be adjusted to compensate for whether the method involves the use of one or both of the M-CSF and GM-CSF.

EXAMPLE 1

The patient was a normal cynomologous monkey, weighing approximately 5 kg, and having a cholesterol level as indicated in Table I below. M-CSF was administered intravenously with a bolus injection followed by continuous infusion at a rate of 35ug/kg/day for days 1-8.

Table I shows that this animal demonstrated a 30% reduction in serum cholesterol, a 27% reduction in HDL cholesterol, and a 55% reduction in LDL cholesterol levels.

TABLE I

| Day | Cholesterol | HDL Cholesterol | LDL Cholesterol |
|-----|-------------|-----------------|-----------------|
| 1   | 147         | 96              | 42              |
| 8   | 103         | 70              | 19              |

EXAMPLE 2

The patient was a normal rhesus monkey, weighing approximately 5 kg, and having a cholesterol level as indicated in Table II below. M-CSF and GM-CSF were administered intravenously with a bolus injection followed by continuous infusion at a rate of 2 ug/kg/day of GM-CSF days 1-7 and a continuous infusion of a combination of 35 ug/kg/day of M-CSF and 20 ug/kg/day of GM-CSF for days 8-15.

Table II shows that this animal demonstrated a 13% reduction in serum cholesterol in response to GM-CSF alone and a further reduction of 22% in response to the combination therapy. The animal's HDL cholesterol was reduced by 22% in response to GM-CSF alone and a further reduction of 12% in response to the combination therapy. LDL cholesterol levels were reduced by 19% in response to GM-CSF alone and further reduced by 33% in response to the combination therapy.

TABLE II

| Day | Cholesterol | HDL Cholesterol | LDL Cholesterol |
|-----|-------------|-----------------|-----------------|
| 1   | 137         | 85              | 37              |
| 8   | 119         | 66              | 30              |
| 15  | 93          | 58              | 20              |

EXAMPLE 3

The patient was a normal rhesus monkey, weighing approximately 5 kg, and having a cholesterol level as indicated in Table III below. M-CSF was administered intravenously with a bolus injection followed by continuous infusion at a rate of 175 ug/kg/day for days 1-8 whereupon M-CSF therapy was stopped.

Table III shows that this animal demonstrated a 30% reduction in serum cholesterol, a 38% reduction in HDL cholesterol, and a 3% reduction in LDL cholesterol in response to the M-CSF therapy. This experiment further shows the effect of removal of the M-CSF therapy and the consequent rise in lipoprotein and cholesterol levels.

TABLE III

| Day | Cholesterol | HDL Cholesterol | LDL Cholesterol |
|-----|-------------|-----------------|-----------------|
| 1   | 126         | 83              | 34              |
| 8   | 88          | 51              | 33              |
| 15  | 133         | 81              | 44              |

What is claimed is:

1. A method for lowering cholesterol levels in a primate by systemically administering to said primate a cholesterol reducing amount of a pharmaceutical composition comprising GM-CSF in admixture with a pharmaceutically acceptable carrier.

* * * * *